United States Patent [19]

Prasad et al.

[11] Patent Number: 5,808,152
[45] Date of Patent: Sep. 15, 1998

[54] SYNTHESIS OF N-(4-FLUOROPHENYL)-2-HYDROXY-N-(1-METHYLETHYL) ACETAMIDE USING SODIUM FORMATE

[75] Inventors: Vidyanatha A. Prasad, LeaWood, Kans.; Jacqueline M. Applegate, Parkville, Mo.; David T. Erdman, Cologne, Germany; Peter E. Newallis, LeaWood, Kans.

[73] Assignee: Bayer Corporation, Pittsburgh, Pa.

[21] Appl. No.: 989,565

[22] Filed: Dec. 12, 1997

[51] Int. Cl.$^6$ .................................................. C07C 233/15
[52] U.S. Cl. .............................................................. 564/202
[58] Field of Search ............................................. 564/202

[56] References Cited

U.S. PATENT DOCUMENTS

| 4,334,073 | 6/1982 | Diehr | 546/245 |
| 5,101,304 | 3/1992 | Schmidt | 548/136 |
| 5,631,403 | 5/1997 | Dierdorf | 564/202 |

FOREIGN PATENT DOCUMENTS

| 3038598 | 5/1982 | Germany | 564/202 |

*Primary Examiner*—Robert Gerstl
*Attorney, Agent, or Firm*—Joseph C. Gil; Carol Marmo

[57] ABSTRACT

The present invention relates to a process for making N-(4-fluorophenyl)-2-hydroxy-N-(1-methylethyl) acetamide. The process includes the steps of (a) reacting 2-chloro-N-(4-fluorophenyl)-N-(1-methylethyl)acetamide with sodium formate to form a reaction mixture that contains N-(4-fluorophenyl)-2-hydroxy-N-(1-methylethyl) acetamideformate; (b) adding an aprotic, aromatic solvent to the reaction mixture; (c) hydrolyzing the N-(4-fluorophenyl)-2-hydroxy-N-(1-methylethyl)acetamideformate in the reaction mixture and (d) recovering N-(4-fluorophenyl)-2-hydroxy-N-(1-methylethyl)acetamide from the organic phase.

29 Claims, No Drawings ions of sodium formate for producing N-(4-fluorophenyl)-2-hydroxy-N-(1-methylethyl)
SYNTHESIS OF N-(4-FLUOROPHENYL)-2-HYDROXY-N-(1-METHYLETHYL) ACETAMIDE USING SODIUM FORMATE

TECHNICAL FIELD OF THE INVENTION

The field of the present invention is the synthesis of hydroxy acetamides. More particularly, the invention relates to methods for synthesizing N-(4-fluorophenyl)-2-hydroxy-N-(1-methylethyl)acetamide.

BACKGROUND OF THE INVENTION

Hydroxy acetamides are useful intermediates in the preparation of thiadiazole acetamide herbicides. An exemplary such herbicide is N-(4-fluorophenyl)-N-(1-methylethyl)-2-[[5-(trifluoromethyl-1,3,4-thiadiazole-2-yl]oxy]acetamide. (See, e.g., U.S. Pat. No. 5,101,034). This thiadiazole acetamide can be made by reacting N-(4-fluorophenyl)-2-hydroxy-N-(1-methylethyl)acetamide with 2-methylsulfonyl-5-trifluoromethyl-1,3,4-thiadiazole (See, e.g., U.S. Pat. No. 5,101,034). Typically, formation of the N-(4-fluorophenyl)-2-hydroxy-N-(1-methylethyl)acetamide is accomplished by converting the corresponding chloride, (i.e., [2-chloro-N-(4-fluorophenyl)-N-(1-methylethyl)acetamide]) to N-(4-fluorophenyl)-2-hydroxy-N-(1-methylethyl)acetamide acetate and then hydrolyzing the acetate intermediate to the final hydroxy acetamide using an alcohol.

U.S. Pat. No. 4,334,073 discloses the production of hydroxy-acetic acid-N-methylamide and hydroxy acetic acid-2-ethyl-piperidine. The methylamide compound is made by reacting chloroacetic acid-N-methylanilide in toluene with sodium acetate and benzyltrimethyl-ammonium chloride to form acetoxy-acetic acid-N-methylanilide and then hydrolyzing that acetate intermediate with methanol to form hydroxy-acetic acid-N-methylamide. A by-product of that reaction, however, is methyl acetate, which must be removed by distillation. In a similar fashion, the piperidine compound is made by reacting chloroacetic acid-N-ethylpiperidine in toluene with sodium acetate and benzyltrimethyl-ammonium chloride to form acetoxy-acetic acid-N-ethylpiperidine and then hydrolyzing that acetate intermediate with methanol to form hydroxy-acetic acid-N-ethylpiperidine. Methyl acetate is also formed as a by-product of that reaction.

There is a need in the art, therefore, for a method of making hydroxy acetamides such as N-(4-fluorophenyl)-2-hydroxy-N-(1-methylethyl)acetamide, which method avoids the formation of methyl acetate and, thus, avoids the need for an additional distillation step.

BRIEF SUMMARY OF THE INVENTION

The present invention provides a process for making N-(4-fluorophenyl)-2-hydroxy-N-(1-methylethyl) acetamide. The process includes the steps of (a) reacting 2-chloro-N-(4-fluorophenyl)-N-(1-methylethyl)acetamide with sodium formate to form a reaction mixture that contains N-(4-fluorophenyl)-2-hydroxy-N-(1-methylethyl) acetamideformate and (b) hydrolyzing the N-(4-fluorophenyl)-2-hydroxy-N-(1-methylethyl) acetamideformate in the reaction mixture to form N-(4-fluorophenyl)-2-hydroxy-N-(1-methylethyl)acetamide. In a preferred embodiment, a slight molar excess of sodium formate relative to 2-chloro-N-(4-fluorophenyl)-N-(1-methylethyl)acetamide is used. In one embodiment, solid sodium formate is used and step (a) is carried out under anhydrous conditions. In accordance with this embodiment, the reaction mixture is heated to a temperature of from about 135° C. to about 140° C. and maintained at this temperature until the 2-chloro-N-(4-fluorophenyl)-N-(1-methylethyl) acetamide is reacted out. Typically, this step requires about 8 hours of heating.

In another embodiment, aqueous sodium formate is used. When aqueous sodium formate is used, it is mixed with 2-chloro-N-(4-fluorophenyl)-N-(1-methylethyl)acetamide to form a reaction mixture which is then heated to a temperature of from about 105° C. to about 110° C., preferably about 107° C. A first portion of water is removed from the reaction mixture, thus, allowing the temperature of the reaction mixture to gradually increase to a temperature of from about 125° C. to about 130° C. A second portion of water is then gradually removed from the reaction mixture, allowing the temperature of the reaction mixture to increase to a temperature of from about 130° C. to about 134° C. The reaction mixture is maintained at this higher temperature (from about 130° C. to about 134° C.) until the 2-chloro-N-(4-fluorophenyl)-N-(1-methylethyl)acetamide is consumed. Typically, removal of the first portion of water takes place over a time period of from about 1 to about 2 hours and removal of the second portion of water takes place over a time period of from about 1 to about 5 hours.

The reaction mixture in either embodiment can optionally contain a phase transfer catalyst. Suitable such catalysts are well known in the art and include triethylamine, myristyltrimethylammonium bromide and tetrabutyl phosphonium bromide.

Following consumption of 2-chloro-N-(4-fluorophenyl)-N-(1-methylethyl)acetamide from the reaction mixture, the mixture is cooled to a temperature of from about 60° C. to about 80° C. An aprotic, aromatic solvent is then added to the cooled reaction mixture. Suitable such solvents include toluene, xylene, cumene and mesitylene. Toluene is most preferred. The reaction mixture is then cooled to a temperature of from about 20° C. to about 30° C., preferably to about room temperature (25° C.).

The N-(4-fluorophenyl)-2-hydroxy-N-(1-methylethyl) acetamideformate in the reaction mixture is then hydrolyzed to N-(4-fluorophenyl)-2-hydroxy-N-(1-methylethyl) acetamide. Hydrolysis is carried out using water or an aqueous alkali. Water or aqueous alkali are added to the reaction mixture to form an aqueous phase and an organic phase. A preferred base is an alkali metal base such as an alkali metal hydroxide or an alkali metal carbonate. Preferred alkali metals are sodium, potassium and lithium. A preferred base is sodium hydroxide, sodium carbonate or potassium carbonate. Sodium hydroxide is most preferred. The molar ratio of base to 2-chloro-N-(4-fluorophenyl)-N-(1-methylethyl)acetamide is from about 0.8:1 to about 1.2:1.

Following hydrolysis, the phases are separated using separation procedures well known in the art. N-(4-fluorophenyl)-2-hydroxy-N-(1-methylethyl)acetamide formed by the process is recovered from the organic phase. Isolation can proceed by any means well known in the art. The yield of N-(4-fluorophenyl)-2-hydroxy-N-(1-methylethyl)acetamide can be enhanced by washing the aqueous phase with additional solvent (e.g., toluene) and then combining the toluene wash with the original organic phase.

DETAILED DESCRIPTION OF THE INVENTION

I. The Invention

This invention relates to processes for making N-(4-fluorophenyl)-2-hydroxy-N-(1-methylethyl)acetamide (FOE-hydroxy). The processes provide for (a) reacting 2-chloro-N-(4-fluorophenyl)-N-(1-methylethyl)-acetamide (FOE-chloride) with sodium formate and (b) hydrolyzing the formed N-(4-fluorophenyl)-2-hydroxy-N-(1-methylethyl)acetamideformate (FOE-formate) to FOE-hydroxy.

II. Process for Making N-(4-fluorophenyl)-2-hydroxy-N-(1-methylethyl)-acetamide Using Solid Sodium Formate In accordance with a present process, 2-chloro-N-(4-fluorophenyl)N-(1-methylethyl)-acetamide (FOE-chloride) is reacted with sodium formate to form a reaction mixture that contains N-(4-fluorophenyl)-2hydroxy-N-(1-methylethyl)acetamideformate (FOE-formate). An aprotic, aromatic solvent is added to the reaction mixture and FOE-formate in the reaction mixture is hydrolyzed to FOE-hydroxy using water or an aqueous alkali.

The FOE-chloride can be prepared by any means known in the art. Means for preparing FOE-chloride include reacting 4-fluoro-isopropylaniline with chloroacetyl chloride. The synthesis of FOE-hydroxy begins with the reaction of FOE-chloride with solid sodium formate in the absence or presence of water. Sodium formate is commercially available. A slight stoichiometric excess of sodium formate is typically used. In accordance with this embodiment, the molar ratio of sodium formate to FOE-chloride is preferably from about 1.01:1 to about 1.25:1 and, more preferably from about 1.05:1 to about 1.10:1

When solid sodium formate is used, the reaction with FOE-chloride can proceed under aqueous or anhydrous conditions. Where anhydrous conditions are used, solid sodium formate is mixed with FOE-chloride and the mixture heated to a temperature of from about 135° C. to about 140° C., until the FOE-chloride is fully consumed or reacted. Typically, this anhydrous reaction requires about 8 hours.

Where aqueous conditions are used, the solid sodium formate and FOE-chloride are mixed with water. The molar ratio of water to FOE-chloride is from about 1.2:1 to about 2:1. Preferably about 1.4 moles of water (25 grams) are mixed with 1 mole of FOE-chloride. The mixture is then slowly heated to a temperature of from about 125° C. to about 130° C., preferably about 130° C. This heating step typically occurs over a period of time ranging from about 1 to about 2 hours. Following the period of gradual heating, the reaction mixture is maintained at a temperature of from about 130° C. to about 134° C. until the FOE-chloride is consumed. Typically, this heating step requires from about 1 to about 4 hours of heating. This heating step should be terminated upon consumption of the FOE-chloride.

The reaction mixture (both aqueous and anhydrous conditions) can optionally contain a phase transfer catalyst. Suitable phase transfer catalysts include triethylamine, myristyltrimethylammonium bromide and tetrabutyl phosphonium bromide. Following disappearance of FOE-chloride from the reaction mixture, the mixture is cooled to a temperature of from about 60° C. to about 80° C. An aprotic, aromatic solvent is then added to the cooled reaction mixture. Suitable such solvents include toluene, xylene, cumene and mesitylene. Toluene is most preferred. The molar ratio of solvent to FOE-chloride is from about 0.5:1 to about 5:1.

Following the addition of solvent, FOE-formate is hydrolyzed to FOE-hydroxy. FOE-formate can be hydrolyzed with water or with an aqueous alkali. If not already present (e.g., anhydrous conditions), water is added to the reaction mixture. Water can be added before or after the addition of solvent. In one embodiment, water is added as part of the cooling step disclosed above.

In accordance with this embodiment, the reaction mixture is rapidly diluted in cold water at a temperature of from about 115° C. to about 125° C. A sufficient amount of water to quench the reaction is used. Typically, from about 10 to about 20 moles of water per mole of FOE-chloride is added to the reaction mixture. In a second step, solvent (e.g., toluene) is added to the diluted reaction mixture at a temperature of about 60° C. to about 80° C. Following the addition of solvent, with or without water addition, the reaction mixture is further cooled to about room temperature (20° C. to about 30° C.). As a result of addition of water, the reaction mixture forms an aqueous and an organic phase.

An aqueous base is preferably used to hydrolyze FOE-formate to FOE-hydroxy. In accordance with this embodiment, following the cooling step, the reaction mixture containing solvent is titrated with a suitable alkali so as to alkalinize the reaction mixture to a pH of from about 11 to about 14 and, preferably to a pH of from about 12 to about 13. Means for determining the amount of base needed to achieve the desired pH are well known in the art and depend, inter alia, on the particular base used.

Any suitable base that results in hydrolysis of the FOE-formate can be used. A preferred base for this titration is an alkali metal base such as an alkali metal hydroxide or an alkali metal carbonate. Preferred alkali metals are sodium, potassium and lithium. A preferred base is sodium hydroxide, sodium carbonate or potassium carbonate. Sodium hydroxide is most preferred. The alkaline pH is maintained until the FOE-formate is substantially completely hydrolyzed to FOE-hydroxy. When sodium hydroxide is used as the base and the pH is about 12.2 to 12.5, a 1 hour reaction period at ambient temperature is typically sufficient.

Following hydrolysis, the phases are separated using procedures well known in the art. FOE-hydroxy formed by the process is recovered from the organic phase. The yield of FOE-hydroxy can be increased by extracting the aqueous phase with the solvent (e.g., toluene) and combining the organic phase extract with the original organic phase prior to recovery.

Recovery can proceed by any means well known in the art. By way of example, the solvent can be stripped off and the resulting molten residue flaked, Alternately, the FOE-hydroxy in solvent can be directly used in subsequent reactions.

III. Process of making FOE-Hydroxy Using Aqueous Sodium Formate

This process includes the steps of reacting FOE-chloride with aqueous sodium formate to form a reaction mixture containing FOE-formate and hydrolyzing the FOE-formate to FOE-hydroxy. When aqueous sodium formate is used, it is mixed with FOE-chloride to form a reaction mixture. The aqueous formate solution can have a sodium formate concentration of from about 5 weight percent to about 50 weight percent. Preferably, the sodium formate concentration is from about 25 weight percent to about 35 weight percent. The reaction mixture is then heated to reflux, a temperature of from about 105° C. to about 110° C., preferably about 107° C.

A first portion of water is removed from the reaction mixture. Removal of water results in the temperature of the reaction mixture gradually increasing to a temperature of from about 125° C. to about 130° C. Typically, removal of the first portion of water takes place over a time period of from about 1 to about 2 hours. A second portion of water is then gradually removed from the reaction mixture, allowing the temperature of the reaction mixture to increase to a temperature of from about 130° C. to about 134° C. Removal of the second portion of water takes place over a time period of from about 1 to about 5 hours. The reaction mixture is maintained at this higher temperature (from about 130° C. to about 134° C.) until the FOE-chloride has been consumed.

Alternately, the first removal of water can be accomplished so as to increase the temperature to about 130° C., followed by maintenance of the reaction mixture at this temperature for about 3 hours. The second removal of water increases the temperature to about 140° C., which temperature is maintained for from about 1 to about 2 hours. Heating should be terminated when the level of FOE-chloride falls below about 0.3%. At this time, the reaction product is predominantly a mixture of FOE-hydroxy (80–85%) and FOE-formate (20–15%).

The following examples illustrate preferred embodiments of the present invention and are not limiting of the specification and claims in any way.

EXAMPLES

Example 1
Synthesis of N-(4-fluorophenyl)-2-hydroxy-N-(1-methylethyl)acetamide Using Aqueous Sodium Formate 229.68 grams (1 mole) of 2-chloro-N-(4-fluorophenyl)-N-(1-methylethyl)acetamide (FOE-chloride) and 238 grams of a 30 weight percent solution of sodium formate in water (1.03 moles of sodium formate) were added to a reaction vessel fitted with a Dean Stark Trap. The vessel was agitated and heated to reflux (ca. 107° C.). Small portions of water were carefully drained from the bottom of the Dean Stark trap, thus permitting the temperature to steadily increase. The incremental removal of water was continued until the reaction temperature reached 130° C. (about 117 g of water was removed at this stage; the water was essentially free of formic acid).

The reaction mixture was heated at 130° C. and the progress of the reaction monitored using HPLC analyses. Small increments of water were continuously removed from the bottom of the Dean Stark trap to maintain a temperature of 130° C. for 3 hours. Maintaining reaction temperature at 130° C. for 3 hours is important. If temperature is raised to 140° C. too quickly, by removing water in an erratic fashion, lumps of sodium formate can result. However, no lumps occur if the temperature is maintained at 130° C. for 3 hours prior to raising it to 140° C. for an hour or so to complete conversion of FOE-chloride.

After maintaining a temperature of 130° C. for 3 hours, the temperature was increased to 140° C.–142° C., with stable reflux, by carefully removing additional water from the bottom of the Dean Stark trap. The reaction mixture was heated for 1–2 hours at 140° C. until HPLC analysis indicated <0.3% FOE-chloride. A total of about 145 g of water containing about 8% by weight of formic acid was collected. The reaction mixture contained about 80% FOE-hydroxy and about 20% FOE-formate at this stage.

The reaction mixture was cooled with agitation and 150 g of toluene was introduced at 60° C.–80° C. The drowned reaction mixture was cooled with agitation to ambient temperature (about 25° C.). A 10% NaOH solution was added to the agitated reaction mixture with cooling while maintaining the pH at 12.2–12.5 for 30 minutes. At this stage, FOE-formate was completely hydrolyzed to FOE-hydroxy (hydrolysis can be followed by G.C. or HPLC analysis).

The organic phase and the aqueous phase were separated. The aqueous phase was washed with 50 g of toluene. The toluene from this wash was combined with the organic phase. Solid FOE-hydroxy was isolated by stripping off the toluene using a rotary evaporator and flaking the molten residue. The product had a purity of 97.4% A.I. (Active Ingredient). The net yield was 97.0%, based on FOE-chloride.

Example 2
Synthesis of N-(4-fluorophenyl)-2-hydroxy-N-(1-methylethyl)acetamide Using Aqueous Sodium Formate 229.68 grams of (1 mole) of 2-chloro-N-(4-fluorophenyl)-N-(1-methylethyl)acetamide (FOE-chloride) and 249.4 grams of a 30 weight percent solution of sodium formate in water (1.08 moles of sodium formate) were added to a reaction vessel fitted with a Dean Stark trap. The vessel was agitated and heated to reflux (ca. 107° C.). Small portions of water were carefully drained from the bottom of the Dean Stark trap, thus permitting the temperature to steadily increase. The incremental removal of water was continued until the reaction temperature reached 130° C. (about 110 g of water was removed at this stage). The time required for this step was between 1 and 2 hours.

The reaction mixture was heated at 130° C.–134° C. and the progress of the reaction followed using HPLC and/or G.C. analyses. Small increments of water were removed from the bottom of the Dean Stark trap as and when necessary to maintain a temperature of 130° C.–134° C. for 4 hours. As the reaction consumes FOE-chloride, the collected water indicates finite amounts of formic acid formed due to the in situ hydrolysis of FOE-formate to FOE-hydroxy. At the end of 4 hours of heating, analysis indicated the absence of chloride, 80–85% FOE-hydroxy, and 20–15% FOE-formate.

The reaction mixture was drowned at 120° C. with 270 g water. Toluene (150 g) was added to the reaction mixture at 60° C.–80° C. The entire mixture was cooled with agitation to ambient temperature (about 25° C.). A 50% NaOH solution was added to the agitated reaction mixture with cooling while maintaining pH at 12.2–12.5 for 1 hour. At this stage, FOE-formate was completely converted to FOE-hydroxy. The phases were separated and FOE-hydroxy recovered as set forth in Example 1. The purity of FOE-hydroxy was 97.5% A.I. and the net yield was 97.2%, based on FOE-chloride Example 3
Synthesis of N-(4-fluorophenyl)-2-hydroxy-N-(1-methylethyl)acetamide Using Aqueous Sodium Formate 229.68 grams (1 mole) of 2-chloro-N-(4-fluorophenyl)-N-(1-methylethyl)acetamide (FOE-chloride) and 272 grams of a 30 weight percent solution of sodium formate in water (1.18 moles of sodium formate) were added to a reaction vessel equipped with a Barrett type distillation receiver. The vessel was agitated and heated to reflux (ca. 107° C.). Small portions of water were carefully drained from the distillation receiver, thus permitting the temperature to steadily increase. The incremental removal of water was continued until the reaction temperature reached 130° C. (about 110 g of water was removed at this stage). The minimum time required to increase the temperature from 107° C. to 130° C. should be 1 hour.

The reaction mixture was heated at 130° C.–134° C. and the progress of the reaction followed using HPLC and/or G.C. analysis. Increments of water were continuously removed from the bottom of the Barrett receiver as and when necessary to maintain a temperature of 130° C.–134° C. (analyses should indicate no chloride, 80–85% FOE-hydroxy and 15–20% FOE-formate). The mixture should not be heated longer than needed.

The reaction mixture was drowned at 120° C. with 270 g water. Toluene (150 g) was added to the reaction mixture at 60° C.–80° C. The entire mixture was cooled with agitation to ambient temperature (about 25° C.). A 50% NaOH solution was added to the agitated reaction mixture with cooling while maintaining pH at 12.2–12.5 for 1 hour. At this stage, FOE-formate was completely converted to FOE-hydroxy. The phases ere separated and FOE-hydroxy recovered as set forth in Example 1.

Example 4
Synthesis of N-(4-fluorophenyl)-2-hydroxy-N-(1-methylethyl)acetamide Using Solid Sodium Formate 229.68 grams (1 mole) of 2-chloro-N-(4-fluorophenyl)-N-(1-methylethyl)acetamide (FOE-chloride), 25 grams of water and 74.8 grams (1.08 moles) of solid sodium formate were added to a reaction vessel equipped with a condenser. The vessel was agitated and heated gradually over 1 to 2 hours to 130° C. The reaction mixture was heated at 130° C.–134° C. for 4 hours and the progress of the reaction followed using HPLC and/or G.C. analysis indicated no FOE-chloride, 80–85% FOE-hydroxy and 15–20% FOE-formate. The mixture should not be heated any longer than necessary.

The reaction mixture was drowned at 120° C. with 270 g water. Toluene (150 g) was added to the reaction mixture at 60° C.–80° C. The entire mixture was cooled with agitation to ambient temperature (about 25° C.). A 50% NaOH solution was added to the agitated reaction mixture with cooling while maintaining pH at 12.2–12.5 for 1 hour. At this stage, FOE-formate was completely converted to FOE-hydroxy. The phases were separated and FOE-hydroxy recovered as set forth in Example 1. The purity of FOE-hydroxy was 97.5% A.I. and the net yield was 97.6%, based on FOE-chloride.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making N-(4-fluorophenyl)-2-hydroxy-N-(1-methylethyl)acetamide comprising the steps of:
   (a) reacting 2-chloro-N-(4-fluorophenyl)-N-(1-methylethyl)-acetamide with solid sodium formate to form a reaction product that contains N-(4-fluorophenyl)-2-hydroxy-N-(1-methylethyl) acetamideformate;
   (b) adding an aprotic, aromatic solvent to the reaction mixture;
   (c) hydrolyzing the N-(4-fluorophenyl)-2-hydroxy-N-(1-methylethyl)acetamideformate in the reaction mixture to N(4-fluorophenyl)-2-hydroxy-N-(1-methylethyl) acetamide; and
   (d) recovering the N-(4-fluorophenyl)-2-hydroxy-N-(1-methylethyl)acetamide.

2. The process of claim 1 wherein the molar ratio of sodium formate to 2-chloro-N-(4-fluorophenyl)-N-(1-methylethyl)acetamide is from about 1.01:1 to about 1.1:1.

3. The process of claim 1 wherein 2-chloro-N-(4-fluorophenyl)N-(1-methylethyl)acetamide and solid sodium formate are admixed, heated to a temperature of from about 135° C. to about 140° C., and reacted at that same temperature until the 2-chloro-N-(4-fluorophenyl)-N(1-methylethyl)acetamide is totally consumed.

4. The process of claim 1 wherein 2-chloro-N-(4-fluorophenyl)N-(1-methylethyl)acetamide, solid sodium formate and water are admixed, heated gradually to a temperature of from about 125° C. to about 130° C., and reacted at a temperature of from about 130° C. to about 134° C. until the 2-chloro-N-(4-fluorophenyl)-N-(1-methylethyl) acetamide is totally consumed.

5. The process of claim 4 wherein the molar ratio of water to 2-chloro-N-(4-fluorophenyl)-N-(1-methylethyl) acetamide is from about 1.2:1 to about 2:1.

6. The process of claim 1 wherein the solvent is toluene, xylene, cumene or mesitylene.

7. The process of claim 6 wherein the solvent is toluene.

8. The process of claim 1 wherein the molar ratio of solvent to 2-chloro-N-(4-fluorophenyl)-N-(1-methylethyl) acetamide is from about 0.5:1 to about 5:1.

9. The process of claim 1 wherein the reaction mixture further comprises a phase transfer catalyst.

10. The process of claim 9 wherein the catalyst is triethylamine.

11. A process for making N-(4-fluorophenyl)-2-hydroxy-N-(1-methylethyl)acetamide comprising the steps of:
   (a) reacting 2-chloro-N-(4-fluorophenyl)-N-(1-methylethyl)-acetamide with aqueous sodium formate to form a reaction product that contains N-(4-fluorophenyl)-2-hydroxy-N-(1-methylethyl) acetamideformate;
   (b) adding an aprotic, aromatic solvent to the reaction mixture to form a aqueous and an organic phase;
   (c) hydrolyzing the N-(4-fluorophenyl)-2-hydroxy-N-(1-methylethyl)acetamideformate in the reaction mixture to N-(4-fluorophenyl)-2-hydroxy-N-(1-methylethyl) acetamide; and
   (d) recovering the N-(4-fluorophenyl)-2-hydroxy-N-(1-methylethyl)acetamide from the organic phase.

12. The process of claim 11 wherein step (a) is accomplished by mixing 2-chloro-N-(4-fluorophenyl)-N-(1-methylethyl)acetamide with an aqueous solution of sodium formate to form a reaction mixture, heating the reaction mixture to reflux, removing a first portion of water from the reaction mixture and allowing the temperature to increase to a temperature of from about 125° C. to about 130° C., removing a second portion of water from the reaction mixture and allowing the temperature to increase to a temperature of from about 130° C. to about 134° C., and maintaining the temperature at from about 130° C. to about 134° C. until the 2-chloro-N-(4-fluorophenyl)-N-(1-methylethyl)acetamide is consumed.

13. The process of claim 12 wherein the first portion of water is removed over a time period of from about 1 to about 2 hours.

14. The process of claim 13 wherein the second portion of water is removed over a time period of from about 1 to about 5 hours.

15. The process of claim 12 wherein the reaction mixture from step (a) is cooled to a temperature of from about 60° C. to about 80° C. and mixed with the solvent.

16. The process of claim 12 wherein the solvent is toluene, xylene, cumene or mesitylene.

17. The process of claim 16 wherein the solvent is toluene.

18. The process of claim 12 wherein the molar ratio of solvent to 2-chloro-N-(4-fluorophenyl)-N-(1-methylethyl) acetamide is from about 0.5:1 to about 5:1.

19. The process of claim 12 wherein the reaction mixture further comprises a phase transfer catalyst.

20. The process of claim 19 wherein the catalyst is triethylamine.

21. The process of claim 12 wherein the product of step (b) is cooled to a temperature of from about 20° C. to about 30° C.

22. The process of claim 12 wherein step (c) is accomplished by titrating the product of step (b) to a pH of from about 11 to about 14 with an alkali metal hydroxide.

23. The process of claim 22 wherein the pH is from about 12 to about 13.

24. The process of claim 23 wherein the alkali metal hydroxide is sodium hydroxide.

25. The process of claim 23 wherein the molar ratio of sodium hydroxide to 2-chloro-N-(4-fluorophenyl)-N-(1-methylethyl)acetamide is from about 0.8:1 to about 1.2:1.

26. The process of claim 12 wherein the aqueous and organic phases are separated after step (c).

27. The process of claim 26 wherein the aqueous phase is extracted with the aprotic, aromatic solvent and the solvent combined with the organic phase before recovery of the N-(4-fluorophenyl)-2hydroxy-N-(1-methylethyl)acetamide.

28. A process for making N-(4-fluorophenyl)-2-hydroxy-N-(1-methylethyl)acetamide comprising the steps of:

(a) reacting 2-chloro-N-(4-fluorophenyl)-N-(1-methylethyl)-acetamide with aqueous sodium formate to form a reaction mixture that contains N-(4-fluorophenyl)-2-hydroxy-N-(1-methylethyl) acetamideformate;

(b) heating the reaction mixture to a temperature of about 107° C.

(c) removing water from the reaction mixture and allowing the temperature to increase to a temperature of from about 130° C. to about 134° C.;

(d) maintaining the temperature at from about 130° C. to about 134° C. until 2-chloro-N-(4-fluorophenyl)-N-(1-methylethyl)-acetamide in the reaction mixture is consumed;

(e) cooling the reaction mixture to a temperature of from about 60° C. to about 80° C.;

(f) adding toluene to the reaction product of step (e) to form an aqueous and an organic phase;

(g) adding sodium hydroxide to the product of step (f);

(h) separating the aqueous and organic phase; and (i) recovering N-(4-fluorophenyl)-2-hydroxy-N-(1-methylethyl)-acetamide from the organic phase.

29. A process for making N-(4-fluorophenyl)-2-hydroxy-N-(1methylethyl)acetamide comprising the steps of:

(a) reacting 2-chloro-N-(4-fluorophenyl)-N-(1-methylethyl)-acetamide with solid sodium formate to form a reaction mixture that contains N-(4-fluorophenyl)-2-hydroxy-N-(1methylethyl) acetamideformate;

(b) heating the reaction mixture to a temperature of from about 130° C. to about 134° C.;

(c) maintaining the temperature at from about 130° C. to about 134° C. until 2-chloro-N-(4-fluorophenyl)-N-(1-methylethyl)-acetamide in the reaction mixture is consumed;

(d) cooling the reaction mixture to a temperature of from about 60° C. to about 80° C.;

(e) adding water and toluene to the reaction product of step (d) to form an aqueous and an organic phase;

(f) adding sodium hydroxide to the product of step (e);

(g) separating the aqueous and organic phase; and (h) recovering N-(4-fluorophenyl)-2-hydroxy-N-(1-methylethyl)-acetamide from the organic phase.

* * * * *